(12) United States Patent
Huang et al.

(10) Patent No.: US 8,068,217 B2
(45) Date of Patent: *Nov. 29, 2011

(54) APPARATUS FOR TESTING COMPONENT CONCENTRATION OF A TEST SAMPLE

(75) Inventors: Yin-Chun Huang, Hsin-Chu (TW); Kuo-Jeng Wang, Kaohsiung (TW)

(73) Assignee: Transpacific Systems, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/877,734

(22) Filed: Sep. 8, 2010

(65) Prior Publication Data

US 2011/0019196 A1 Jan. 27, 2011

Related U.S. Application Data

(63) Continuation of application No. 12/368,237, filed on Feb. 9, 2009, now Pat. No. 7,817,255.

(51) Int. Cl.
*G01N 33/48* (2006.01)

(52) U.S. Cl. .......................................... 356/39; 356/445

(58) Field of Classification Search .................... 356/39, 356/402, 445, 448
See application file for complete search history.

(56) References Cited

U.S. PATENT DOCUMENTS

| 6,945,943 | B2 | 9/2005 | Pugh |
| 7,817,255 | B2 * | 10/2010 | Huang et al. .................... 356/39 |
| 2003/0069509 | A1 | 4/2003 | Matzinger et al. |

* cited by examiner

*Primary Examiner* — Roy M Punnoose
(74) *Attorney, Agent, or Firm* — Stolowitz Ford Cowger LLC

(57) ABSTRACT

An apparatus with a combination of a point light source and a single lens is provided. The present apparatus includes a point light source, a photodetector and a lens. The lens is placed in the same side of the point light source and the photodetector in order that the light emitting from the point light source is focused onto a target area of an object through the lens. The reflected light from the target area is focused onto the photodetector through the lens. The present apparatus can qualitatively and quantitatively monitor a content of a specific component of a tested solution. The geometric relationship of the point light source, the photodetector and the single lens can improve a measuring resolution of the present apparatus.

20 Claims, 2 Drawing Sheets

APPARATUS FOR TESTING COMPONENT CONCENTRATION OF A TEST SAMPLE

This application is a continuation of U.S. application Ser. No. 12/368,237, now U.S. Pat. No. 7,817,255, filed Feb. 9, 2009, which claims priority from U.S. application Ser. No. 10/718,567, filed Nov. 24, 2003, now U.S. Pat. No. 7,508,498, and Taiwanese Application No. 091138111 filed Dec. 31, 2002, which are incorporated herein by reference.

BACKGROUND OF THE INVENTION

1. Field of the Invention

The present invention relates to an apparatus capable of detecting a small-size object or a small target area of an object, and more particularly to an apparatus with a combination of a point light source and a single lens.

2. Description of the Prior Art

The quantification of chemical and biochemical components in colored aqueous fluids, in particular colored biological fluids such as whole blood and urine and biological fluid derivatives such as serum and blood plasma, is of ever-increasing importance. Important applications exist in medical diagnosis and treatment and in the quantification of exposure to therapeutic drugs, intoxicants, hazardous chemicals and the like. In some instances, the amounts of materials being determined are either so miniscule in the range of a microgram or less per deciliter or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. The diabetic patients usually measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

In a method currently and widely used, a sample of fresh whole blood (typically 20~40 μl) is placed on an ethylcellulose-coated reagent pad containing an enzyme system having glucose oxidase and peroxidase activity. The enzyme system reacts with glucose and releases hydrogen peroxide. The pad also contains an indicator that reacts with the hydrogen peroxide in the presence of peroxidase to give a color proportional in intensity to the sample's glucose level. Another popular blood glucose test method employs similar chemistry but in place of the ethylcellulose-coated pad employs a water-resistant film through which the enzymes and indicator are dispersed.

In both cases the sample is allowed to remain in contact with the reagent pad for a specified time (typically one minute). Then in the first case the blood sample is washed off with a stream of water while in the second case it is wiped off the film. The reagent pad or film is then blotted dry and evaluated. The evaluation is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator calorimetric determinations in that their result is based on an absolute color reading, which is in turn related to the absolute extent of reaction between the sample and the test reagent. The fact that the sample must be washed or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing can give low results and underwashing can give high results.

Another problem that often exists in simple lay-operator calorimetric determination is the necessity for initiating a timing sequence when blood is applied to a reagent pad. A user will typically have conducted a finger stick to obtain a blood sample and will then be required to simultaneously apply the blood from the finger to a reagent pad while initiating a timing circuit with his or her other hand, thereby requiring the use of both hands simultaneously. This is particularly difficult since it is often necessary to insure that the timing circuit is started only when blood is applied to the reagent pad. Both of the prior methods require additional manipulations or additional circuitry to achieve this result.

Accordingly, it is an intention to provide means for monitor a content of a specific component in a colored fluid such as a blood sample, which can overcome the drawbacks of the prior methods.

SUMMARY OF THE INVENTION

It is one objective of the present invention to provide an apparatus with a combination of a point light source and a single lens, which can be used to detect a small-size object or a small target area of an object.

It is another objective of the present invention to provide an apparatus with a combination of a point light source and a single lens, which satisfies requirements of light-weighted, miniaturized, and easily carrying with.

It is still another objective of the present invention to provide an apparatus with a combination of a point light source and a single lens, in which the lens provides a light-focusing effect, therefore, a light source with highly light intensity is not necessitated.

It is yet another objective of the present invention to provide an apparatus with a combination of a point light source and a single lens, which is provided with a simple configuration and merely needs few elements so that it is easily manufactured and production-cost saved.

It is a further objective of the present invention to provide an apparatus with a combination of a point light source and a single lens, which can be used to detect a specific component contained in a probe zone of a test strip.

It is still a further objective of the present invention to provide an apparatus with a combination of a point light source and a single lens, which can be used to detect a specific component of a biological specimen, and easily operated.

It is still a further objective of the present invention to provide an apparatus with a combination of a point light source and a single lens, in which the lens provides a light-focusing effect capable of improving measuring resolution of the apparatus.

In order to achieve the above objectives of this invention, the present invention provides an apparatus with a combination of a point light source and a single lens. The present apparatus includes a point light source, a photodetector and a lens. The lens is placed in the same side of the point light source and the photodetector in order that the light emitting from the point light source is focused onto a target area of an object through the lens. The reflected light from the target area is focused onto the photodetector through the lens. The lens provides twice light-focusing effects. The geometric relationship of the point light source, the photodetector and the single lens thus can improve a measuring resolution of the present apparatus. The present apparatus is provided with a simple configuration and few elements so as to save an occupying space and conveniently carry with. The production cost is also reduced.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENTS

The present invention provides an apparatus with a combination of a point light source and a single lens. The present apparatus includes a point light source, a photodetector and a lens. The lens is placed in the same side of the point light source and the photodetector in order that the light emitting from the point light source is focused onto a target area of an object through the lens. The reflected light from the target area is focused onto the photodetector through the lens. The present apparatus can be used as a reflectance instrument for detecting a small-size object or a small target area of an object. A content of a specific component contained in the object thus can be determined in accordance with the reflectance of the light reflected from the object detected by the present apparatus. The present apparatus can be used to detect the reflectance of a light reflected from a colored area of a test strip occurring due to contact with a tested solution. A content of a specific component of the tested solution can be determined in accordance with the reflectance of the light reflected the colored area of the test strip.

Figure 1:
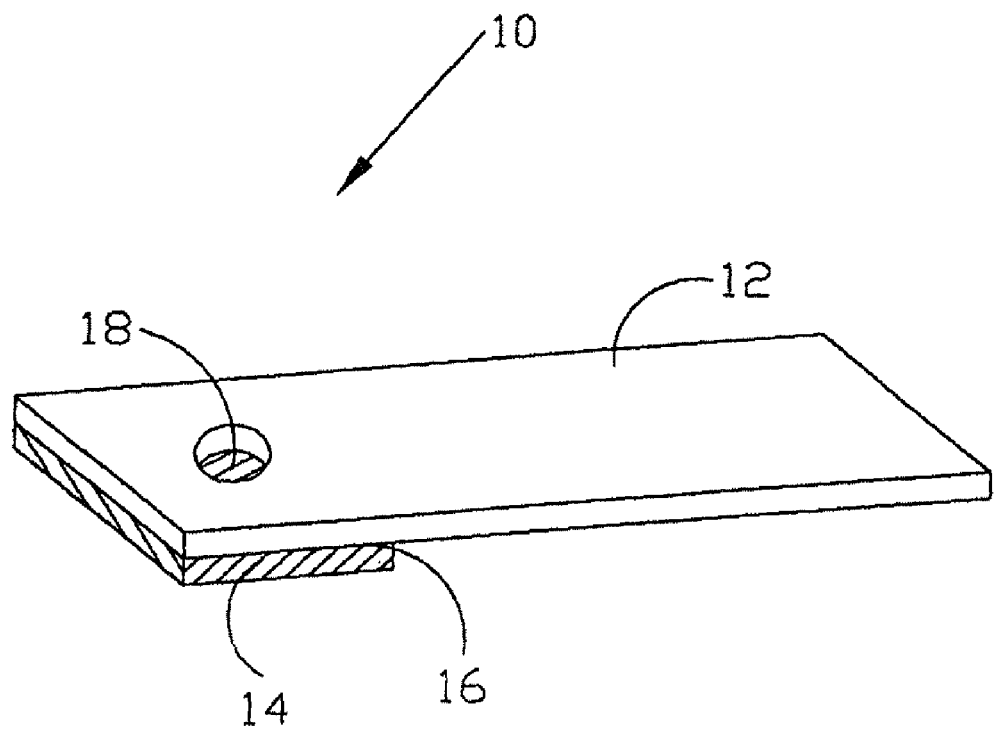
FIG. 1 is a schematic perspective view of a test strip.

FIG. 1 is a schematic perspective view of a test strip 10 used for monitoring a specific component of a tested solution. The test strip 10 includes a strip substrate 12 and a reagent pad 14. The reagent pad 14 is attached onto a test surface of the strip substrate 12 with an adhesive 16. The reagent pad 14 includes an enzyme system and an indicator. The enzyme system contains an oxidase reacting with the specific component of the tested solution to release hydrogen peroxide and a peroxidase to induce the hydrogen peroxide reacting with the indicator to produce a colored light-absorbing material. An opening 18 is formed in a sample surface of the strip substrate 12 opposite to the test surface. The tested solution is applied unto the reagent pad 14 through the opening 18. When the enzyme system of the reagent pad 14 contains glucose oxidase and peroxidase, glucose of a blood sample applied unto the reagent pad 14 through the opening 18 is catalyzed by the glucose oxidase to release hydrogen peroxide. Under catalyzed by peroxidase, the hydrogen peroxide reacts with the indicator to produce a colored light-absorbing material in the reagent pad 14 corresponding to the test surface of the strip, substrate 12. The glucose concentration of the blood sample is proportional to the color intensity, i.e. the shade of the color, of the colored light-absorbing material. The colored light-absorbing material changes the reflectance of the light reflected from the reagent pad 14. The glucose concentration of the blood sample can be determined in accordance with the reflectance of the light reflected from the colored light-absorbing material. When the enzyme system of the reagent pad 14 contains cholesterol oxidase, which catalyzes cholesterol to release hydrogen peroxide. The test strip 10 can be used to monitor a content of cholesterol in a blood sample. Therefore, the kind of the specific component of the tested solution to be detected depends on the design of the enzyme system. In accordance with the above-mentioned, the reflectance of the light reflected from the colored light-absorbing material of the reagent pad 14 is inversely proportional to a content of the specific component. The present apparatus detects the reflectance of the light reflected from the colored light-absorbing material of the reagent pad 14. The content of the specific component of the tested solution is accordingly determined.

The present apparatus and applications thereof will be described in detail in accordance with preferred embodiments as follows.

Figure 2:
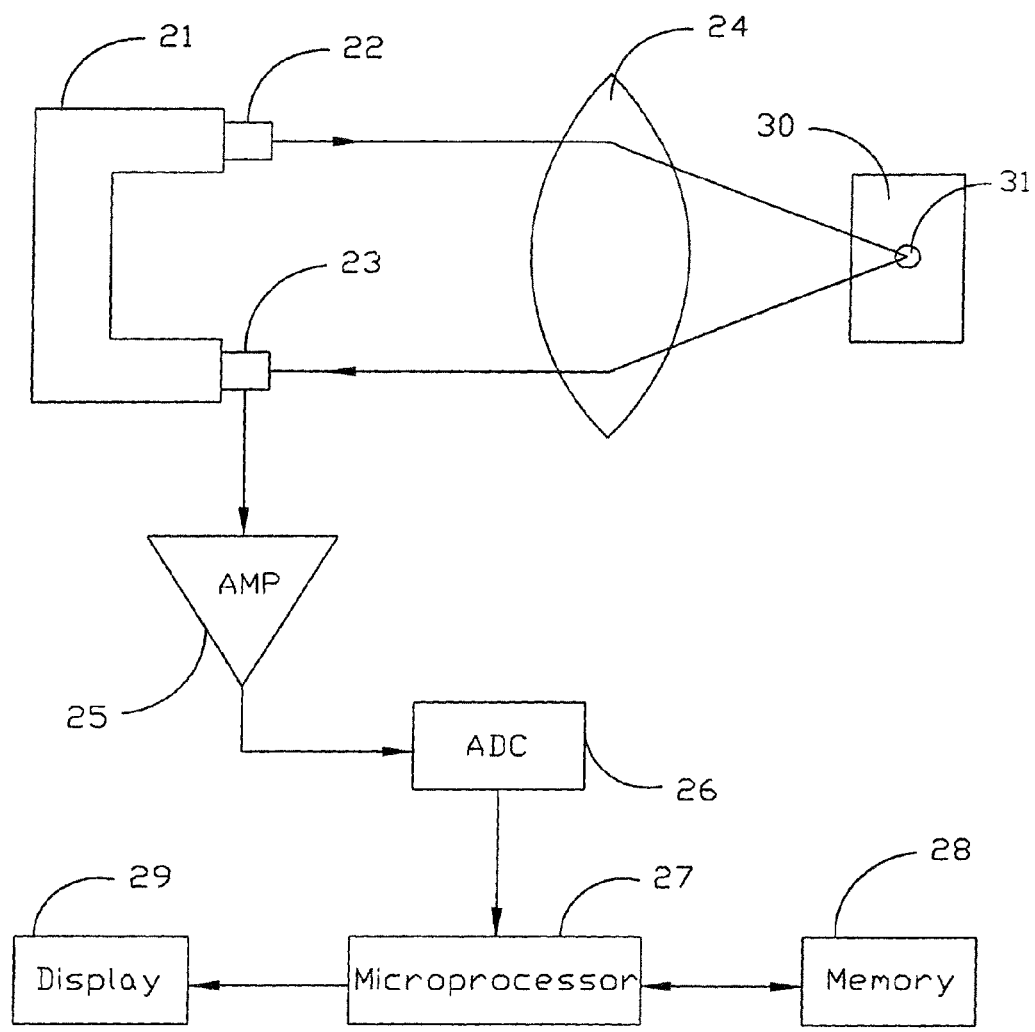
FIG. 2 is a schematic functional block diagram of a reflectance instrument according to a first preferred embodiment of the present invention.

FIG. 2 is a schematic functional block diagram of a reflectance instrument associated with a first preferred embodiment of the present apparatus. The reflectance instrument associated with the present apparatus includes a holder 21, a point light source 22, a photodetector 23, a lens 24, an amplifier (AMP) 25, an analog to digital converter (ADC) 26, a microprocessor 27, a memory 28 and a display 29. The point light source 22 is disposed at a first end of the holder 21, and the photodetector 23 is disposed at a second end of the holder 21. The first end and the second end are on the same side of the holder 21. The lens 24 is placed at the same side of the point light source 22 and the photodetector 23 in order that the light emitting from the point light source 22 is focused onto a light-absorbing area 31 of an object 30 through the lens 24. It is preferable that the object 30 is placed at a focal position of the lens 24. The reflected light from the light-absorbing area 31 of the object 30 is then focused onto the photodetector 23 through the lens 24. The light-absorbing area 31 of the object 30 contains a colored light-absorbing material capable of absorbing the light emitting from the point light source 22. The color intensity, i.e. the shade of color, of the colored light-absorbing material is proportional to a content of a specific component causing the colored light-absorbing material. As a consequence, the reflectance of the light of the point light source 22 reflected from the light-absorbing area 31 is inversely proportional to the content of the specific component. Referring again to FIG. 1, the object 30 can be a test strip 10 having a colored light-absorbing area occurring due to a specific component of a tested solution applied unto the reagent pad 14 of the test strip 10 through the opening 18. The photodetector 23 generates a response current in response to the light of the point light source 22 reflected from the light-absorbing area 31 of the object 30. In the present preferred embodiment, the point light source 22 can be a light emitting diode (LED), and the photodetector 23 can be a photodiode, a charge-coupled device or a complex metal oxide semiconductor sensor (CMOS sensor).

The response current generated from the photodetector 23 in response to a reflected light from the light-absorbing area 31 of the object 30 is converted to an analog voltage by an amplifier (AMP) 25. The analog voltage is converted to a set of digital signals through an analog to digital converter (ADC) 26, and then sent to a microprocessor 27. The microprocessor 27 serves the following control functions: 1) timing for the entire system; 2) reading of the output of the analog to digital converter 26; 3) together with a program stored in a memory 28 to calculate the reflectance measured at specified time intervals and storing it in the memory 28; 4) calculating a concentration value of the specific component corresponding to the light-absorbing area 31 of the object 30. The concentration value is then displayed by a display 29, such as a liquid crystal display (LCD).

A second preferred embodiment of the present invention includes elements like those of the first preferred embodiment except for the design of the point light source. In the second preferred embodiment, the point light source is designed to radiate a light with a first wavelength and a light with a second wavelength. The light with the first wavelength can be absorbed by the tested solution contained in the light-absorbing area 31 of the object 30, and whether the sampling amount of the tested solution is sufficient can be determined by the reflectance of the light with the first wavelength reflected from the light-absorbing area 31. For example, when the amount of the tested solution applied unto the light-absorbing area 31 of the object 30 is insufficient, the present apparatus detects the reflectance of the light with the first wavelength merely little less than the reflectance of the light with the first wavelength upon that the tested solution is not applied unto the object 30. For example, when the reflectance of the light with the first wavelength is not less than a predetermined value, the analog to digital converter 26 could send one-bit digital signal "0" to the microprocessor 27. The microprocessor 27 then sends an alarm signal to remind the user the sampling amount of the tested solution is insufficient. When the amount of the tested solution applied unto the light-absorbing area 31 of the object is sufficient, the reflectance of the light with the first wavelength detected by the present apparatus is significantly decreased compared to that upon that the tested solution is not applied to the object 30. For example, when the reflectance of the light with the first wavelength detected by the present apparatus is less than the predetermined value, the analog to digital converter 26 could send one-bit digital signal "1" to the microprocessor 27. Then, the microprocessor 27 controls the point light source 22 radiates the light with a second wavelength through the lens to focus unto the light-absorbing area 31 of the object 30. The colored light-absorbing material contained in the light-absorbing area 31 can absorb the light with the second wavelength. The colored light-absorbing material may be caused by the specific component of the tested solution applied unto the object 30. Therefore, the content of the specific component can be determined in accordance with the reflectance of the light with the second wavelength detected by the present apparatus.

The lens 24 of the present apparatus utilized in the reflectance instrument provides twice light-focusing effect so as to improve the measuring resolution of the reflectance instrument. Furthermore, the present apparatus has a simple configuration and fewer elements, the purpose of cost down can be attained, and the requirements of light-weighted, miniaturized, and conveniently carrying with are also complied with.

The embodiments are only used to illustrate the present invention, not intended to limit the scope thereof. Many modifications of the embodiments can be made without departing from the spirit of the present invention.

What is claimed is:

1. An apparatus, comprising:
   one or more light sources configured to irradiate a test apparatus comprising a test sample with a first wavelength and a second wavelength;
   one or more photodetectors configured to receive a first reflected light comprising the first wavelength and to receive a second reflected light comprising the second wavelength; and
   a processor configured to analyze the first reflected light to determine a sampling amount of the test sample comprising a specific component, wherein the processor is further configured to analyze the second reflected light to determine a concentration of the specific component in the test sample.

2. The apparatus of claim 1, wherein the sampling amount is determined when a reflectance value of the first reflected light is less than a predetermined value.

3. The apparatus of claim 2, wherein the predetermined value is based on a reflectivity of the first reflected light without the test sample.

4. The apparatus of claim 1, wherein the processor is configured to determine the concentration of the specific component based on a reflectance value of the second reflected light.

5. The apparatus of claim 1, further comprising a single lens configured to focus both the first reflected light and the second reflected light onto the one or more photo detectors.

6. The apparatus of claim 5, wherein the single lens is further configured to focus light comprising the first wavelength and light comprising the second wavelength onto the test apparatus.

7. An apparatus, comprising:
   means for irradiating a test sample applied to a test apparatus, wherein the test sample is irradiated with both a first wavelength and a second wavelength;
   means for receiving a first reflected light comprising the first wavelength, wherein the means for receiving is further configured to receive a second reflected light comprising the second wavelength;
   means for analyzing the first reflected light to determine a sampling amount of the test sample comprising a specific component; and
   means for analyzing the second reflected light to determine a concentration of the specific component in the test sample.

8. The apparatus of claim 7, wherein the means for irradiating comprises means for irradiating the test sample with different wavelengths of light.

9. The apparatus of claim 7, wherein the means for irradiating is configured to separately irradiate the test sample with the first wavelength followed by the second wavelength.

10. The apparatus of claim 7, wherein the means for analyzing the first reflected light comprises means for comparing a reflectance value of the first reflected light with a predetermined value.

11. The apparatus of claim 7, wherein the means for analyzing the second reflected light comprises means for determining the concentration of the specific component based on a reflectance value of the second reflected light.

12. The apparatus of claim 7, further comprising means for focusing a light comprising the first wavelength onto the test sample, wherein the means for focusing is also configured to focus the first reflected light onto the means for receiving.

13. The apparatus of claim 7, further comprising means for focusing a light comprising the second wavelength onto the test sample, wherein the means for focusing is also configured to focus the second reflected light onto the means for receiving.

14. The apparatus of claim 7, further comprising means for focusing the first reflected light and the second reflected light onto the means for receiving.

15. A method, comprising:
irradiating a test apparatus comprising a test sample with a first wavelength;
receiving a first reflected light comprising the first wavelength;
analyzing the first reflected light to determine a sampling amount of the test sample comprising a specific component;
irradiating the test apparatus with a second wavelength;
receiving a second reflected light comprising the second wavelength; and
analyzing the second reflected light to determine a concentration of the specific component.

16. The method of claim 15, wherein the test apparatus is irradiated with the second wavelength in response to determining the sampling amount of the test sample.

17. The method of claim 15, further comprising comparing a reflectance value of the first reflected light with a predetermined value, wherein the predetermined value is based on a reflectivity of the test apparatus without the test sample.

18. The method of claim 15, further comprising sequentially focusing both the first reflected light and the second reflected light onto a sensor using a single focusing lens.

19. The method of claim 15, further comprising sending an alarm signal in response to determining that a reflectance value associated with the first reflected light is more than a predetermined value.

20. The method of claim 15, further comprising sequentially focusing light comprising the first wavelength and light comprising the second wavelength onto the test apparatus using a single focusing lens.

* * * * *

UNITED STATES PATENT AND TRADEMARK OFFICE
CERTIFICATE OF CORRECTION

| | | |
|---|---|---|
| PATENT NO. | : 8,068,217 B2 | Page 1 of 1 |
| APPLICATION NO. | : 12/877734 | |
| DATED | : November 29, 2011 | |
| INVENTOR(S) | : Huang et al. | |

It is certified that error appears in the above-identified patent and that said Letters Patent is hereby corrected as shown below:

On the title page, item (75), under "Inventors", in Column 1, Line 1, delete "Hsin-Chu" and insert -- Hsinchu --, therefor.

In Column 3, Line 27, delete "DESCRIPTION" and insert -- DETAILED DESCRIPTION --, therefor.

In Column 4, Line 1, delete "strip," and insert -- strip --, therefor.

In Column 6, Line 28, in Claim 5, delete "photo detectors." and insert -- photodetectors. --, therefor.

Signed and Sealed this
Twelfth Day of June, 2012

David J. Kappos
*Director of the United States Patent and Trademark Office*